US00PP25481P3

(12) United States Plant Patent
Schoone

(10) Patent No.: US PP25,481 P3
(45) Date of Patent: Apr. 28, 2015

(54) ***PHALAENOPSIS* ORCHID PLANT NAMED 'BRAVERY'**

(50) Latin Name: *Phalaenopsis hybrida*
Varietal Denomination: Bravery

(71) Applicant: Floricultura, Heemskerk (NL)

(72) Inventor: René Schoone, Assendelft (NL)

(73) Assignee: Floricultura, Heemskerk (NL)

( * ) Notice: Subject to any disclaimer, the term of this patent is extended or adjusted under 35 U.S.C. 154(b) by 230 days.

(21) Appl. No.: 13/573,579

(22) Filed: Sep. 26, 2012

(65) Prior Publication Data

US 2013/0081175 P1 Mar. 28, 2013

Related U.S. Application Data

(60) Provisional application No. 61/540,314, filed on Sep. 28, 2011.

(30) Foreign Application Priority Data

Sep. 30, 2011 (NL) ..... PBR OPS848

(51) Int. Cl.
*A01H 5/00* (2006.01)
*A01H 5/02* (2006.01)

(52) U.S. Cl.
CPC ..... *A01H 5/02* (2013.01)
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — Foley & Lardner LLP; Sunit Talapatra

(57) ABSTRACT

A new and distinct *Phalaenopsis* plant named 'Bravery' particularly characterized by flowers which are white with purple spots and a purple mark in the center; the labellum is white, yellow and purple; plants which may be propagated economically and uniformly using tissue culture; plants which produce more than one inflorescence; long and sturdy inflorescences; and relatively short, dark-green foliage.

3 Drawing Sheets

Latin name of the genus and species of the plant claimed: *Phalaenopsis hybrida.*

Variety denomination: 'Bravery'.

BACKGROUND OF THE INVENTION

The present invention relates to a new and distinct cultivar of *Phalaenopsis* plant, botanically known as *Phalaenopsis* of the Orchidaceae family, and hereinafter referred to by the cultivar name 'Bravery'.

*Phalaenopsis* comprises a genus of about 55 species of herbaceous perennials many of which, or the hybrids thereof, are suitable for cultivation in the home or greenhouse. *Phalaenopsis* is predominantly epiphytic or rock-dwelling, and is native to tropical Asia, the Malay Archipelago, and Oceania. The species typically has 2-ranked, fleshy, oblong or elliptic leaves affixed to a short central stem (monopodial growth), which vary in size from 5 to 8 inches to over 2 feet. The leaves may be entirely green or mottled with silver grey.

*Phalaenopsis* orchids, often referred to as 'Moth Orchids' in the horticultural trade, are frequently used to furnish cut flowers for the florist trade or sold as flowering potted-plants for home or interiorscape.

*Phalaenopsis* produces upright or pendent lateral racemes, often with many showy flowers which open in succession beginning with the lowermost. The flowers possess three sepals and three petals; the lateral ones being alike. The lowermost petal, called the labellum, is three-lobed and is often more brightly-colored than the other flower segments. Flower colors include various shades of pink, white, yellow and red-brown.

*Phalaenopsis* orchids are typically propagated from seeds. Asexual propagation of *Phalaenopsis* is often done from off-shoots which frequently arise from the lower bracts of the inflorescence. The resulting plants are detached from the mother plant and may be planted in a suitable substrate.

The new *Phalaenopsis* 'Bravery' is a product of a controlled breeding program conducted by the inventors, René Schoone, in Strengweg, Heemskerk, The Netherlands. The objective of the breeding program was to develop a new *Phalaenopsis* cultivar particularly characterized by its attractive and unique colored flowers, economical propagation via tissue culture, rapid growth, and a plant dimension suitable for packaging and shipping to the market.

The new *Phalaenopsis* 'Bravery' originated from a cross made by the inventor in 1999 in Strengweg, Heemskerk, The Netherlands. The female or seed parent is the *Phalaenopsis* cultivar designated 'Ching Hua Spring', unpatented. The male or pollen parent is the *Phalaenopsis* cultivar designated 'Wonder Mountain', unpatented. The new *Phalaenopsis* 'Bravery' was discovered and selected by the inventor as a single flowering plant within the progeny of the stated cross in a controlled environment in 2006 in Strengweg, Heemskerk, The Netherlands.

Asexual reproduction of the new *Phalaenopsis* cultivar by tissue culture (mericloning) was first performed in July, 2007 in Cieweg 13, Heemskerk, The Netherlands, and has demonstrated that the combination of characteristics as herein disclosed for the new cultivar are firmly fixed and retained through successive generations of asexual reproduction. The new cultivar asexually reproduces true to type.

BRIEF DESCRIPTION OF THE INVENTION

The following traits have been repeatedly observed and are determined to be unique characteristics of 'Bravery', which in combination distinguish this *Phalaenopsis* as a new and distinct cultivar:

1. flowers which are white with purple spots and a purple mark in the center; the labellum is white, yellow and purple;
2. plant produces more than one inflorescence;
3. plants may be propagated economically and uniformly using tissue culture;
4. inflorescences are long and sturdy; and
5. relatively short, dark-green foliage.

In comparison with the parental cultivars of 'Bravery', the female parent 'Ching Hua Spring' has white colored flowers with many purple spots/marks. The size of the flower is about 8 cm. The male parent 'Wonder Mountain' has white colored flowers which are about 11 cm in size, whereas the flowers of 'Bravery' are white with purple spots/marks and flowers are about 9.5 cm in size.

Presently, the commercial cultivar to which 'Bravery' can be meaningfully compared is 'FLOR169431', (U.S. Plant patent application Ser. No. 13/987,999). The flowers of 'FLOR169431' are white with in the center a purple mark whereas the flowers of 'Bravery' are white with a purple mark in the center, but also some purple marks on the sepals en petals. Also the shape and size of the flower differs.

BRIEF DESCRIPTION OF THE PHOTOGRAPHS

The accompanying photographs illustrate the overall appearance of the new *Phalaenopsis* 'Bravery' showing the colors as true as is reasonably possible with colored reproductions of this type. Colors in the photographs may differ slightly from the color values cited in the detailed botanical description, which accurately describe the color of 'Bravery'.

DETAILED BOTANICAL DESCRIPTION

Figure 1:
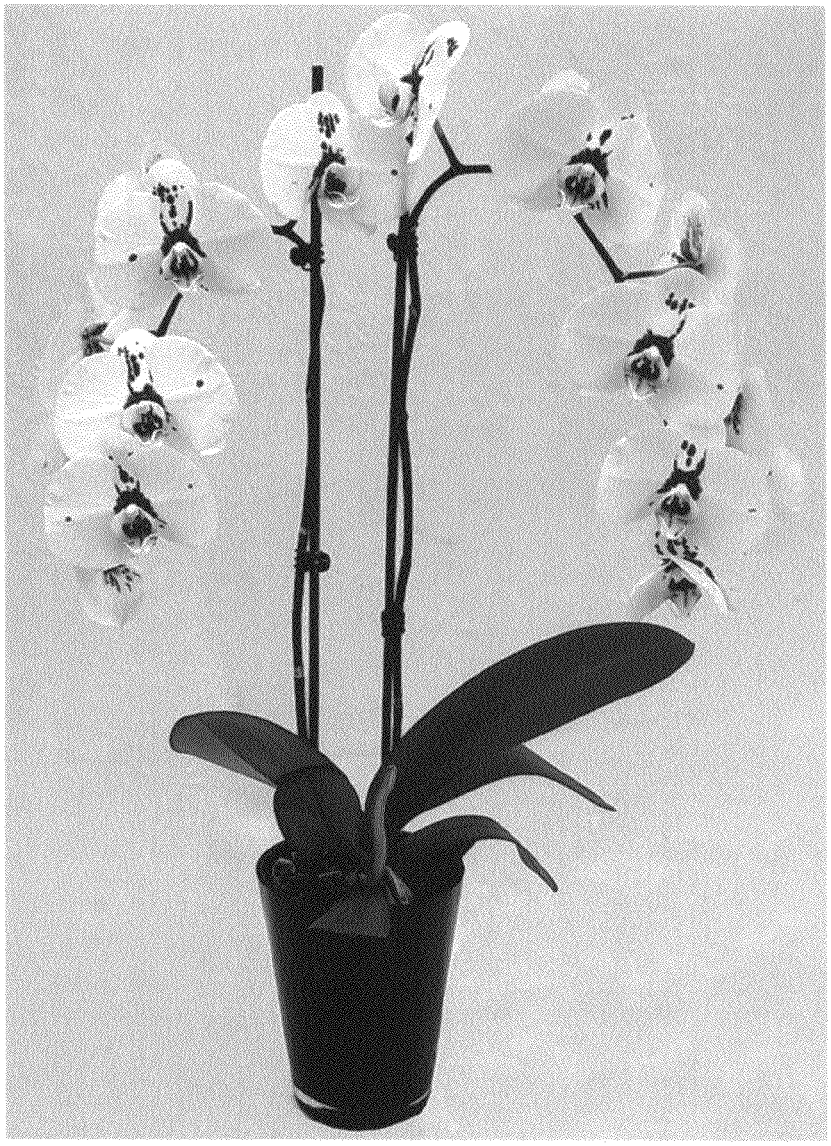
FIG. 1 shows a side view perspective of a typical flowering plant of 'Bravery' in a 12 cm pot, at 16 months of age.

The new *Phalaenopsis* cultivar 'Bravery' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe plants of 'Bravery' as grown in a greenhouse in Strengweg, Heemskerk, The Netherlands, under conditions which closely approximate those generally used in commercial practice. Initially, the ideal temperature to grow plants of 'Bravery' is 27° C. during the day and at night. Then, during the flowering phase of 'Bravery', the ideal growing temperature is 20-22° C. during the day and 18° C. at night. Light levels for growing 'Bravery' are a minimum of 5,000 lux and a maximum of 10,000 lux. A balanced fertilizer with level of 200 ppm N, 87 ppm P, 168 ppm K is applied. Duration of growth of 'Bravery' from potting size is between 10 and 14 months.

Color references are made to The Royal Horticultural Society Colour Chart (R.H.S.), 2007 edition, except where general colors of ordinary significance are used. Color values were taken under daylight conditions at approximately noon in Zaandammerweg, Assendelft, The Netherlands. The age of the 'Bravery' plants described is 12 months after potting.

Classification:

*Botanical.—Phalaenopsis hybrida.*

Parentage:

*Female or seed parent.—Phalaenopsis* cultivar designated 'Ching Hua Spring', unpatented.

*Male or pollen parent.—Phalaenopsis* cultivar designated 'Wonder Mountain', unpatented.

Propagation:

*Type.*—Tissue culture (mericloning).

*Rooting habit and description.*—Fleshy; approximately 4 mm-5 mm wide and green in color (RHS 137A); freely branching. It takes 12 weeks for plants growing in tissue culture to initiate roots.

Plant:

*Size at maturity.*—Height (from bottom of pot to top of highest flower): about 57 to 61 cm. Spread: about 50 to 70 cm.

*Growth habit.*—Standard; green leaves (RHS N137B) and relatively normal raceme.

*Vigor.*—Moderate.

*Crop time.*—Following asexual propagation, at about 26 weeks 2 leaves appear; at about 30 weeks 3-4 leaves appear; after a cold treatment of about 4-8 weeks at a temperature of about 19° C. about 1 to 2 racemes with flowers appear.

Foliage:

*Quantity per plant.*—About 6 to 9 leaves are produced before flowering.

*Arrangement and attachment.*—Half up/horizontal and on two sides.

*Overall shape of leaf.*—Oval, tip is blunt and asymmetric.

*Texture (both surfaces).*—Smooth and leathery.

*Pubescence.*—None.

*Base.*—Acute.

*Margin.*—Entire.

*Mature leaf length.*—About 19 to 23 cm.

*Mature leaf width.*—About 8 to 10 cm.

*Mature leaf thickness.*—About 1.5 mm.

*Mature leaf color (upper surface).*—Green (RHS N137B).

*Mature leaf color (under surface).*—Main color is yellow/green (RHS 146B), edges and veins are purple (RHS N179A).

*Venation.*—Pattern: parallel. Color of mid vein: upper surface green (RHS N137A). Under surface purple (RHS N79A).

Raceme:

*Quantity per plant.*—About 1 to 2.

*Number of flowers per raceme.*—About 5 to 8.

*Length.*—About 70 to 75 cm.

*Diameter.*—About 4 to 6 mm.

*Strength.*—Strong.

*Aspect.*—Upright.

*Texture.*—Glabrous and smooth.

*Color.*—Green (RHS 147A).

*Internode.*—Length: about 35 to 50 mm.

Inflorescence description:

*Appearance*.—Upright to slightly pendant, racemose inflorescence with bilaterally symmetrical flowers that open in succession beginning with the lowermost flower.

*Buds*.—Height (from base to tip): about 15 to 30 mm. Diameter (at midpoint): about 15 to 25 mm. Shape: egg-shaped. Color: Main color is yellow/green (RHS 145B), at the base purple (RHS N79A) and purple spots (RHS N79A). Orientation: same as flowers (forward facing).

*Flowering time*.—For an untreated plant (flowering plant that has not undergone cold-treatment where the plant grows at a temperature of 18° C. to 19° C. for about 4 to 8 weeks after a period of about 30 weeks at a temperature of 25° C.), 1 to 2 racemes appear with flower buds and flowers. First flowers can be expected approximately 4 to 6 months after planting a plant with a leaf diameter of 3 to 5 cm. Flowers persistent.

*Flowering longevity*.—On the plant: about 4 to 6 months; lastingness of cut flowers: has not been observed.

*Fragrance*.—No fragrance.

Figure 2:
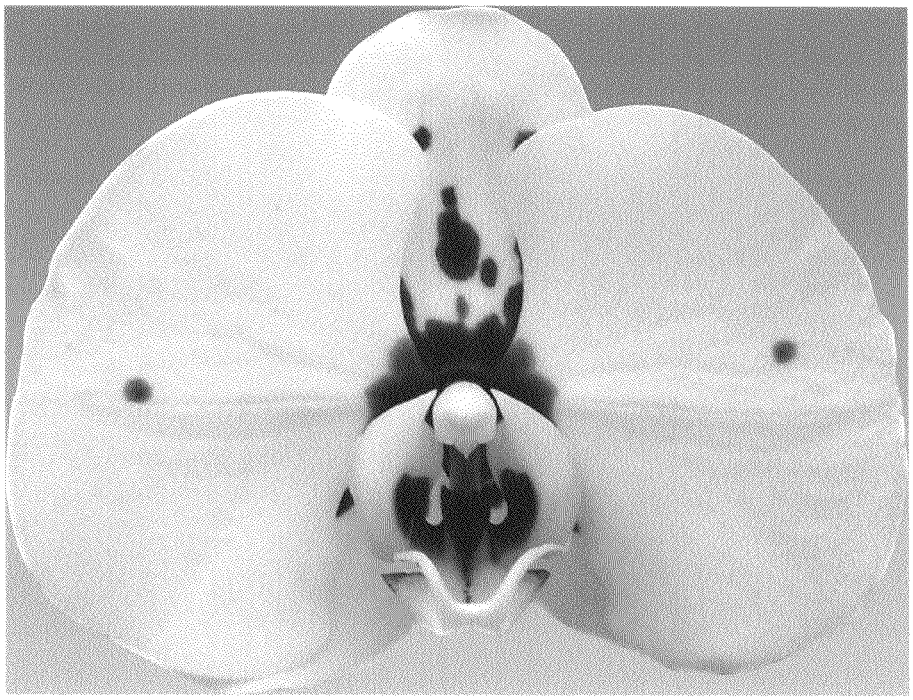
FIG. 2 shows a close-up view of the typical flower of 'Bravery'.
Figure 3:
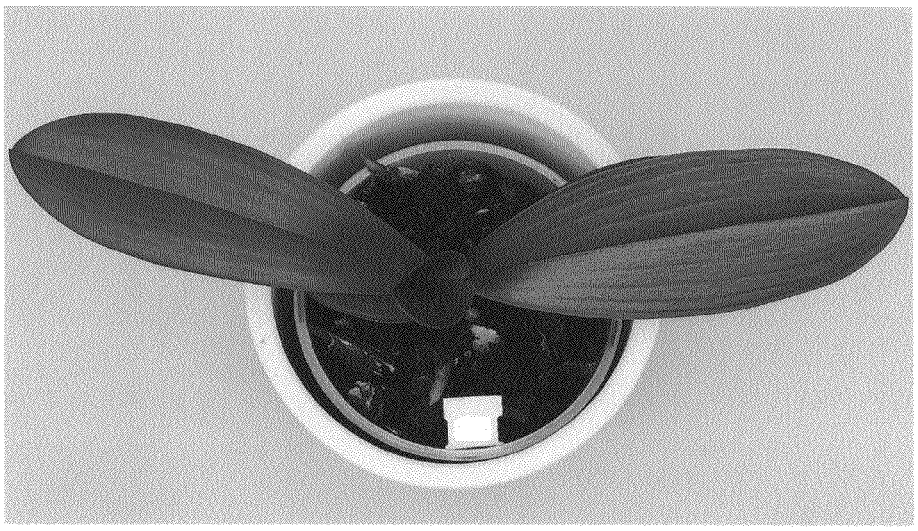
FIG. 3 shows a close-up view of the typical leaves of 'Bravery'.

*Flower*.—Rate of opening: Flowers fully opened about 2 to 3 days after petal and sepal separation. Orientation at opening: slanted upward and outward. Shape: Typical shape of *Phalaenopsis* orchid; see FIG. 2. Size (of single bloom): Height: about 80 mm. Diameter: about 95 mm. Quantity and arrangement: three petals and three sepals that are trimerous, overlapping and arranged in 2 whorls. Petals are more pronounced than sepals.

*Petals*.—Arrangement: Inner whorl comprises 3 petals: 2 lateral petals and labellum. 2 lateral petals: Overall shape: broadly ovate and weakly cupped. Apex: oval. Margin: entire and weakly undulate. Base: broadly ovate. Length: about 60 mm. Width: about 45 mm. Texture: Upper surface: smooth and satiny. Under surface: smooth and satiny. Color (when fully opened): Upper surface: Main color is white (RHS NN155C), base is purple (RHS N79A) with lighter purple edges (RHS N78A) with 1 to 3 purple dots (RHS N79A) with lighter edges (RHS N78A). Under surface: White (RHS NN155C). Labellum: Overall shape: 3-lobed with 2 prominent callosities at central junction of the lateral lobes and base of the midlobe. Lateral lobes of labellum fold upward about the column; the midlobe extends forward and is terminated by 2 filiform appendages at the apex. Lateral lobes of the labellum are ovate in shape while the midlobe is triangular with a bump and a rib on it. Margin: entire and weakly undulate. Length: about 25 mm. Width (not flattened): about 20 mm. Depth of tube (made from lateral lobes): about 15 mm. Texture: Upper & under surface: smooth and satiny. Color (when fully opened): Mid lobe: main color is white (RHS NN155C). At the base green/yellow (RHS 1B) with purple spots (RHS 71A). Lateral lobes: main color is white (RHS NN155C), lower edges are yellow (RHS 2A) with a yellow/green border (RHS 1A). At the base purple (RHS N79A) turning into red/purple (RHS 71A).

*Cirrhi*.—Long. Color: white (RHS NN155C).

*Pestle* (*Callosities*).—Length: about 5 mm. Width (not flattened): about 6 mm. Height: about 11 mm. Color: purple (RHS N77A), at the base white (RHS N155D) with yellow edge (RHS 12A).

*Sepals*.—Arrangement: Outer whorl comprises 3 sepals. Overall shape: elliptical and weakly cupped. Length: about 40 mm. Width: about 30 to 36 mm. Texture: Upper & under surface: smooth and satiny. Color (when fully opened): Main color is white (RHS NN155C) with a green/yellow haze (RHS 1C), at the base purple (RHSN79A) with purple spots and edges (RHS N78A). Underside: Main color is white (RHS N155C) with yellow/green haze (RHS 1C), purple spots (RHS 77A) and the end of the vein red/purple (RHS 73A).

*Pedicel*.—Length: about 35 to 50 mm. Diameter: about 4 mm. Texture: glabrous and smooth. Color: the base is purple (RHS N77A), in the middle RHS 142C and close to the flower red/purple (RHS 73D).

Reproductive organs:

*Arrangement*.—The stamens, style and stigmas are fused into a single, short structure called the column, possessing one terminal anther with pollen grains united into a pollinia, which are covered by an anther cap. The stigma is located under the column behind the pollinia. The ovary is inferior with three carpels present. The plant has not produced seed.

*Column*.—Length: about 9 mm. Diameter: about 7 mm. Color: white (RHS NN 155C).

*Pollinia*.—Quantity: Two. Size: about 1 mm. Color: yellow/orange (RHS 23A).

*Ovary*.—Length: about 4 mm. Diameter: about 6 mm. Color: white (RHS NN155C).

Disease/pest resistance/susceptibility: No specific resistance or susceptibility observed.

Temperature tolerance: Tolerant to a low temperature of about 15° C. and to a high temperature about 30° C.

What is claimed is:

1. A new and distinct *Phalaenopsis* plant named 'Bravery', as illustrated and described herein.

* * * * *